United States Patent

Rørvik et al.

[11] Patent Number: 5,874,118
[45] Date of Patent: Feb. 23, 1999

[54] FEED FOR FARMED FISH AND METHOD TO PROVIDE FISH OF HIGH QUALITY BY USE OF ADDITIONAL COMPONENTS IN STANDARD FEED

[75] Inventors: Kjell Arne Rørvik, Oslo; Svein Hallbjørn Steien, Heer, both of Norway

[73] Assignee: Norsk Hydro ASA, Oslo, Norway

[21] Appl. No.: 817,609

[22] PCT Filed: Oct. 20, 1995

[86] PCT No.: PCT/NO95/00193

§ 371 Date: Jun. 16, 1997

§ 102(e) Date: Jun. 16, 1997

[87] PCT Pub. No.: WO96/12415

PCT Pub. Date: May 2, 1996

[30] Foreign Application Priority Data

Oct. 21, 1994 [NO] Norway .................................. 944028

[51] Int. Cl.⁶ ...................................................... A23K 1/00
[52] U.S. Cl. .................................. 426/69; 426/2; 426/805
[58] Field of Search .................. 426/69, 2, 805

[56] References Cited

U.S. PATENT DOCUMENTS

| | | | |
|---|---|---|---|
| 3,911,117 | 10/1975 | Ender | 424/180 |
| 3,930,018 | 12/1975 | Akasaki et al. | 424/322 |
| 5,262,184 | 11/1993 | Rorvik et al. | 426/72 |

FOREIGN PATENT DOCUMENTS

| | | |
|---|---|---|
| 0495264 | 7/1992 | European Pat. Off. |
| 574974 | 12/1993 | European Pat. Off. |
| 96 12415 | 5/1996 | WIPO |

OTHER PUBLICATIONS

Kaushik, et al., "Utilization of Dietary Urea in Rainbow Trout", *Ann. Nutr. Metab.* 27:94–106 (1983).

Knyazeva, "Importance of urea as a nitrogen supplement in food for rainbow trout", *Chemical Abstracts*, vol. 87, No. 13, Sep. 26, 1977, Abstract No. 100984p.

Brizinova, "Effect of phosphatides and carbamide on the assimilation of protein feed by rainbow trout." *Chemical Abstracts*, vol. 69, No. 1, Jul. 1, 1968, Abstract No. 1078t.

Dabrowski, "Study of the use of nonprotein nitrogen compounds in the feeding of carp (*Cyprinus carpio*). Feed characteristics, fish growth, and feed use." *Chemical Abstracts*, vol. 92, No. 3, Jan. 21, 1980, Abstract No. 21041d.

*Primary Examiner*—Chhaya D. Sayala
*Attorney, Agent, or Firm*—Wenderoth, Lind & Ponack, L.L.P.

[57] ABSTRACT

Feed for fish containing standard fish feed, 3–60 g urea/kg feed and 5–20 g trimethylamine oxide/kg feed. Such feed is useful to provide sea farmed fish having salt-water tolerance, reduced tendency for skin ulcers and improved effect of pigments in the feed.

3 Claims, 5 Drawing Sheets

Control(C)   Experimental(E)

Control(C)  Experimental(E)

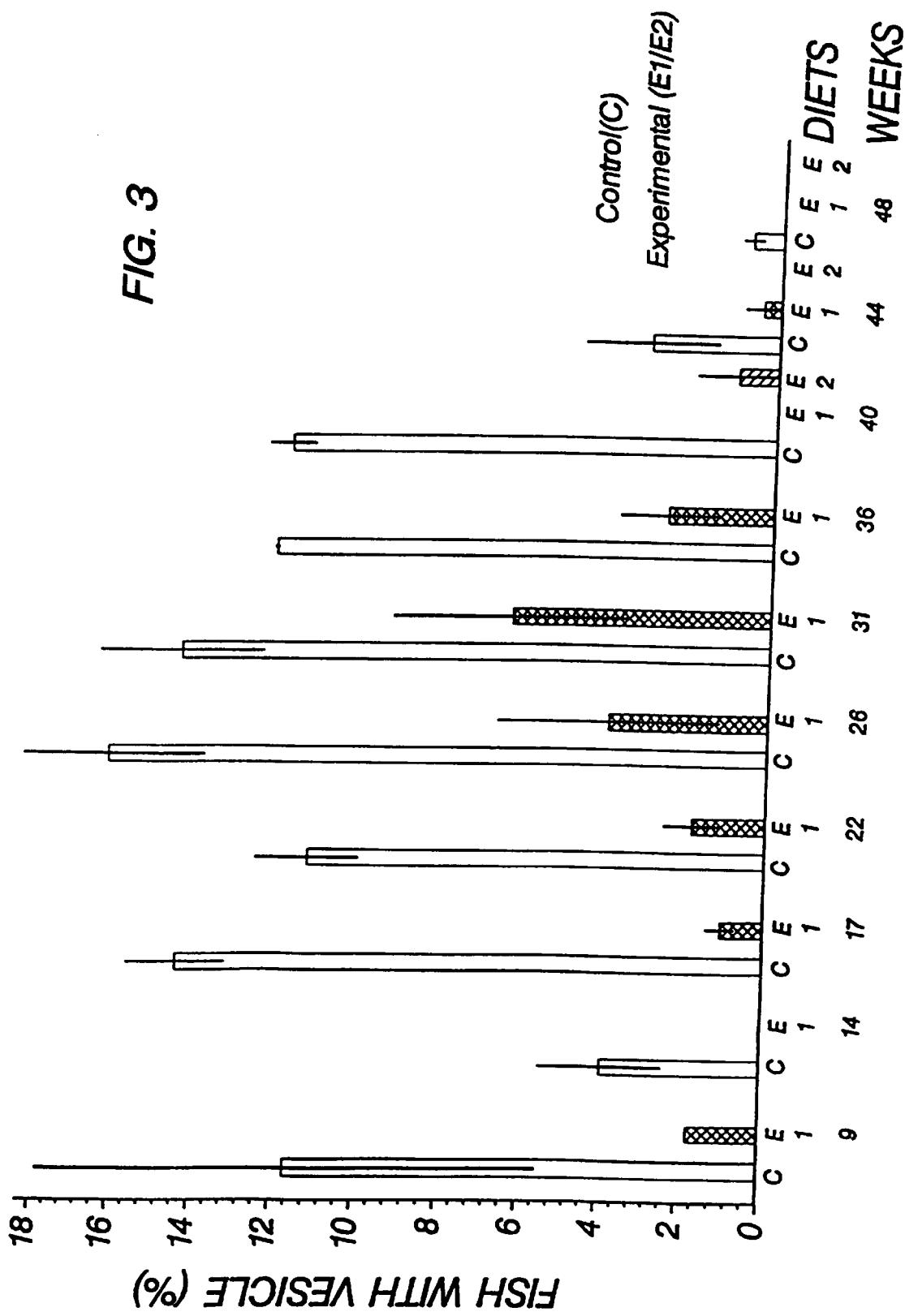

FEED FOR FARMED FISH AND METHOD TO PROVIDE FISH OF HIGH QUALITY BY USE OF ADDITIONAL COMPONENTS IN STANDARD FEED

BACKGROUND OF THE INVENTION

The present invention relates to a feed for farmed fish. The invention further comprises a method to provide fish of high quality and use of additional components to prepare said feed.

The main purpose of the invention is to contribute to low cost production of high quality salmonides like rainbow trout and Atlantic salmon.

For the aquaculture industry it has long been an economic problem that farmed fish like salmon and trout do not naturally achieve the same strongly red colour as the wild species. Such farmed fishes are palely red, unless large amount of synthetic red pigments are supplemented to the feed, and therefore not as attractive as the wild fish to the customers.

In a world wide investigation, it is shown that next to product freshness the colour of the flesh is the most important quality criteria for the Atlantic salmon and thus fundamental for market acceptance and price (Koteng, 1992; Markedsundersøkelse Norsk Laks. FNL. Bergen. Norway). Hence, to obtain an image and high market value of salmonides with regard to characteristic red or pink flesh pigmentation, pigments like astaxanthin are added to the feeds to make the fish more red.

The deposition rate of astaxanthin in the muscle of salmonides depends on several factors. These include the dietary source of astaxanthin, the concentration of astaxanthin, dietary fat content, and physiological factors such as fish size, growth rate, maturation, and genetic factors (Torrissen et al., 1995; <<Astaxanthin deposition in the flesh of Atlantic salmon; Salmo salar L., in relation to dietary astaxanthin concentration and feeding period>>, in Aquaculture nutrition, 77–84).

The supplement of pigments in the diets of salmonides represents a considerable part of the feed cost. In Norway for example, the astaxanthin supplement in Atlantic salmon diets represents about 20% of the feed costs, or close to 10% of the total production costs. This is mainly due to the low retention of dietary astaxanthin. Thus, increasing the dietary level of astaxanthin from 60 to 100 mg/kg gives an insignificant increase in muscle concentration of only 3% (Torrissen et al., 1995), and several studies have shown that increasing the dietary concentration of astaxanthin above 40 mg/kg gives a significantly reduced relative astaxanthin retention (%). Hence, to improve quality and to reduce production costs, it would be of great importance to develop a feed which improve the retention of dietary astaxanthin.

Another problem in fish farming is development of ulcers on the fish skin, especially for big salmon in the winter when the temperature is low, and for $0^+$-smolt the first winter at sea. Ulcers increase mortality and reduce the price since slaughtered fish with ulcers are down classified from superior to production quality.

M. Staumes et al. (Aquaculture, vol. 90, 1990; <<Distanced, water-filled stomach in sea farmed rainbow trout>>., pp. 333–343) have reported that a large amount of rainbow trout which are cultured in salt water develop a considerably enlarged abdomen. This is connected to a great enlarged stomach containing water and fat. There is today no treatments for fish suffering from this disease. In addition to the above mentioned problems, the rainbow trout, and in some cases also the salmon, have problems with the fat digestibility. The condition characterised as <<fat belching>> is put in association with the occurrence of water-filled stomach (O. Einen, Hovedoppgave ved NLH, 1989: <<Eit studium av vassbuk hos regnbogeaure>>).

The main object of the present invention is therefore to provide a fish feed which improves the quality of the fish with regard to colour, ulcers and fat digestibility.

The inventors wanted to examine the effect of urea and/or trimethylamine oxide (TMAO) in the feed with regard to promotion of growth and saltwater tolerance of the fish. Commercial fish feed supplemented with trimethylamine oxide (TMAO) is known from for example our own Norwegian patent no. 920083 where TMAO is added to the feed to achieve an optimum level of bio-available dietary iron, and French patent no. 2561871 where TMAO was supplemented to make the feed more appetising to the fish. From U.S. Pat. No. 3,930,018 using isobutylidene diurea as an additional component in the feed for pisciculture for the purpose of promoting growth is known. Furthermore, the utilization of dietary urea in rainbow trout has been studied by Kaushik. et al. in 1983 (<<Utilization of dietary urea in rainbow trout>>, Ann. Nutr. Metab., 27: 94–106).

SUMMARY OF THE INVENTION

The invention provides fish feed which comprises standard fish feed, 3–60 g urea/kg feed and optionally 5–20 g trimethylamine oxide/kg feed; and a method to provide sea farmed fish having salt-water tolerance, reduced tendency for skin ulcers and improved effect of pigments in the feed, by feeding the fish with such fish feed.

During our studies concerning the effect of urea and/or TMAO supplemented to a standard feed, i.e. a feed comprising proteins, lipids, carbohydrates and one or more further components like fillers, adhesives, preservatives, vitamins, minerals and pigments, an unexpected positive short term effect on salt water tolerance was observed. It was surprisingly found that addition of urea in contrast to addition of TMAO, lead to stable osmolality in the fish for months.

Analyses of urea in the blood and the muscle in small rainbow trout were performed (FIG. 1A). Additionally, analyses of urea in the muscle of big rainbow trout and Atlantic salmon were performed (FIG. 1B). The analyses showed that urea did not accumulate in the fish.

More surprisingly and unexpected it was observed that the colour of the fish flesh for the fish fed with feed where urea and TMAO were added, was significantly more red than for the fish fed with the control feed not having additional amounts of urea and TMAO. Colour analyses of the flesh of rainbow trout showing significantly stronger colour were performed (FIG. 2). Thus, an optimised effect of the pigment in the feed is achieved.

It was further surprisingly observed that development of ulcers on the skin of the fish fed with the urea and/or TMAO supplemented feed was considerably less than for fish fed with the control feed not having urea and TMAO added. This is further shown in FIG. 3 where experimental data of vesicles in the fish skin of rainbow trout are expressed.

It was accordingly shown that supplement of urea and/or TMAO to the feed had positive effect with regard to reduction of fat droplets on the sea surface produced by the fish, and thus reduction of fat belching, even when high energy feed was used (FIG. 4).

The total TMAO content in the feed should be in the range 5–20 g/kg feed, preferentially 5–15 g/kg. Additional components with similar methyl donating properties as TMAO, for instance betain or choline, can be added to the standard fish feed instead of TMAO, to improve the fat metabolism in farmed fish.

The content of urea in the feed should be in the range 3–60 g/kg feed, preferentially 3–30 g/kg.

The scope of the invention and its special features are as defined in the attached claims.

The invention is further described and explained in the following description of the figures, the attached figures and the examples.

BRIEF DESCRIPTION OF DRAWINGS

FIGS. 1A–4 show the results of analyses of experiments involving the fish feed of the present invention and is further described below.

FIG. 1. Shows levels of urea in plasma and flesh of rainbow trout during the first 36 weeks in sea water (A), and levels of urea in flesh of rainbow trout and Atlantic salmon after a weight gain from 2.0 to 4.5 kg and from 0.6 to 1.2 kg, respectively, in sea water (B).

FIG. 2. Shows colour analyses of rainbow trout fed control or experimental diets.

FIG. 3. Shows development of vesicle in the skin of rainbow trout fed control diet compared to experimental diets.

FIG. 4. Shows variation in fat belching for rainbow trout.

FIGS. 1A and 1B show about the same accumulation of urea in the flesh of Atlantic salmon as in rainbow trout, and apparently independent of the amount of dietary urea. Addition of dietary urea led to a stable, but small increase in plasma urea of only 0.5 mM. Hence, dietary urea is totally excreted.

FIG. 2 shows significantly increased redness, yellowness and chromaticity for rainbow trout fed experimental diets supplemented with urea compared to fish fed control diet without any supplement. A significant increase in both redness and yellowness, and therefore in chromaticity, but not in hue, indicate that supplement of dietary urea improves the retention of dietary astaxanthin.

FIG. 3 shows that supplement of dietary urea in the experimental feeds had a highly significant and positive effect on development of vesicle in the skin of rainbow trout. Vesicles developed into open sores after 36 weeks are only present among fish fed the control diet.

FIG. 4 shows a significantly reduced number of fat droplets in net pens where rainbow trout fed experimental diets supplemented with either TMAO or TMAO and urea were kept. Hence, the positive effect was due to TMAO and the addition of urea did not interfere with the TMAO's effect on fat belching.

DETAILED DESCRIPTION OF THE INVENTION

In all experiments the same commercial BioOptimal® recipe (see table 1) was used as basis feed. Said feed is present in different sizes, i.e. pellets having diameter 3.5 mm, 4.5 mm, 6.5 mm, 9.0 mm and 12.0 mm.

TABLE 1

| Contents: | Size: 3.5 mm 4.5 mm | Size: 6.5 mm 9.0 mm 12.0 mm |
|---|---|---|
| Water (max.), % | 10.0 | 10.0 |
| Crude protein, % (fish meal based) | 42.0 | 40.0 |
| Fat (Soxhlet), % | 26.0 | 30.0 |
| Carbohydrates, % (NFE) | 15.5 | 13.5 |
| Fibre, % | 0.6 | 0.6 |
| Ash, % | 7.8 | 7.8 |
| Astaxanthin, mg/kg | 27.5–50.0 | 50.0–60.0 |
| Gross Energy, MJ/kg | 22.8 | 23.60 |

The control feed was coated with pure water, while the experimental feeds were coated with a water solution of urea alone, a mixed solution of urea and TMAO, or TMAO alone. The amount of supplement was 1% for all components, individually. After coating, the feeds were air dried for 2 days before being administered to the fish.

Finally, all tests were performed in duplicated net pens at AKVAFORSK's sea site, Averøy, apart from two studies of flesh colour in commercial fish farms where the experimental feed was not supplemented by coating, but during production of the feed. Ten fish per net pen were randomly sampled for analyses and the statistics were performed by GLM in SAS.

EXAMPLE 1

This was a study on accumulation of dietary urea in rainbow trout as well as in Atlantic salmon. The study was performed by recurrent sampling of rainbow trout after transfer to sea (FIG. 1A), and on rainbow trout and Atlantic salmon after a weight gain from 2.0 to 4.5 kg and from 0.6 to 1.2 kg, respectively (FIG. 1B).

Figure 1A:
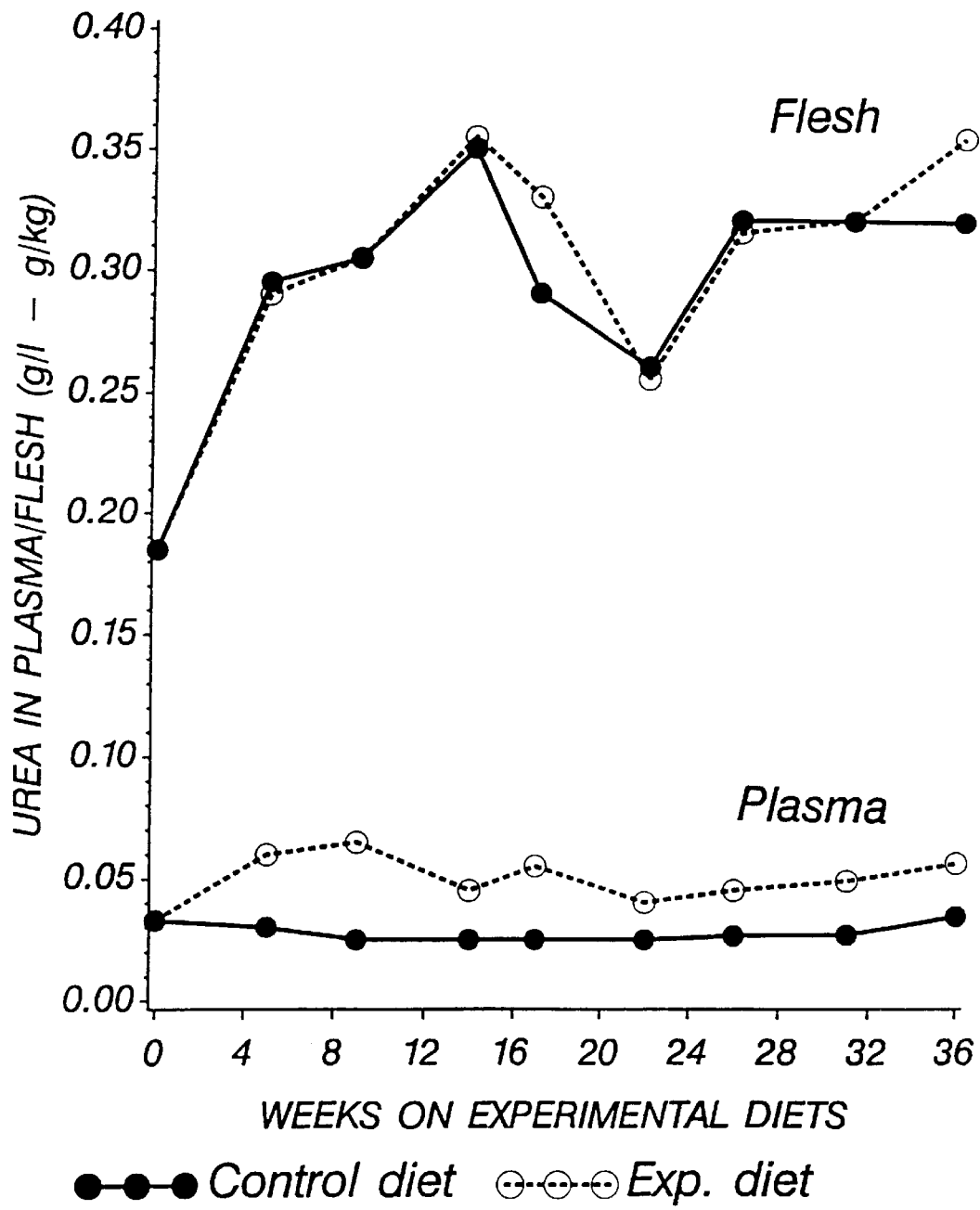
Figure 1B:
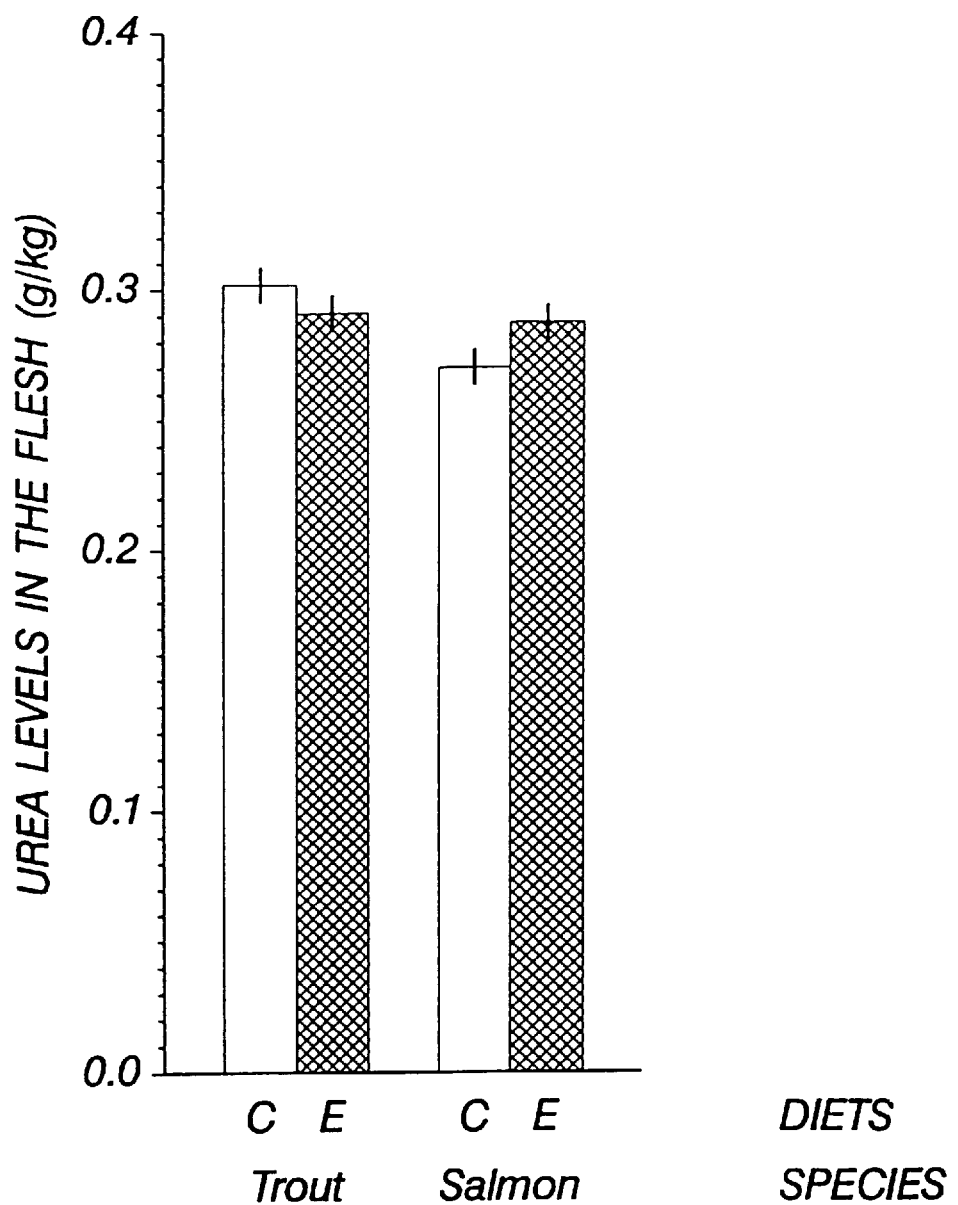
Figure 2A:
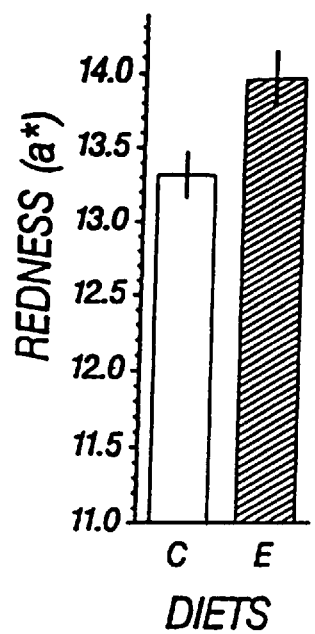
Figure 2B:
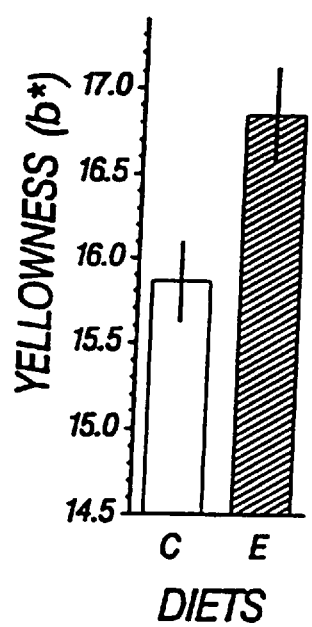
Figure 2C:
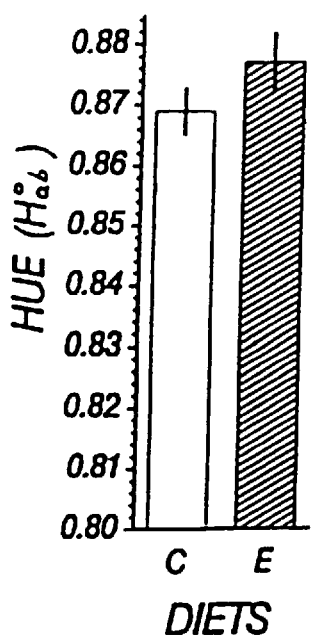
Figure 2D:
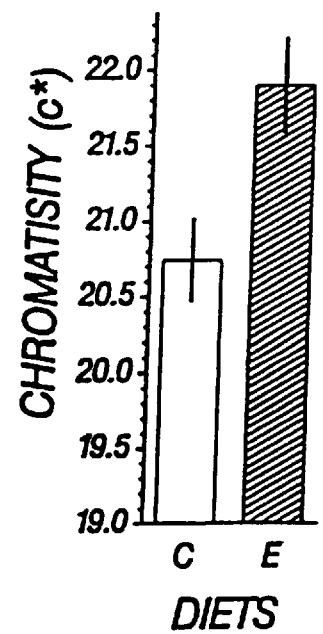

Sampling of plasma and flesh from 10 fish per pen each 6 weeks after sea transfer always showed about the same amount of urea in the flesh whether the rainbow trout were fed experimental diet supplemented with urea and TMAO or control feed (FIG. 1A). The same result was also observed in trials with rainbow trout fed urea and TMAO and Atlantic salmon fed urea alone after doubling of the body weight (FIG. 1B). A significant increase in plasma urea in rainbow trout fed urea supplement, compared to the control fish was observed. However, this increase is probably without any practical significance since it correspond to an increase of only 0.5 mM. It can therefore be concluded that the addition of urea in the feeds is not leading to accumulation of urea in the fish and that urea is not an active osmolytt in rainbow trout. This is according to the observations of Kaushik et al. (1983). They concluded that dietary urea is totally excreted leading to no beneficial effect on nitrogen balance, and since the circulating levels of urea in the blood were low, the osmoregulatory role of urea in teleost is considered to be of limited importance.

EXAMPLE 2

In the trials with rainbow trout in example 1 it was surprisingly observed that when the fish were slaughtered at the end of the experiment, those fed experimental diet had a more red flesh than those fed control feed. This was documented by measurements of flesh colour by Minolta Chroma Meter. The instrument records the values L* (lightness), a* (redness) and b* (yellowness). $H°_{ab}$ (hue) and c* (chromaticity) were calculated as $H°_{ab} = \arctan(b^*/a^*)$ and $c^*=\sqrt{a^{*2}+b^{*2}}$). $H°_{ab}=0$ is pure red. Colour analyses were performed at the cutlet side just behind the end of the dorsal fin (Norwegian Quality Cut). In addition, rainbow trout were sampled from two commercial farms testing the idea for only 6 and 10 weeks (body weight 0.6 to 0.8 kg). In the commercial farms, the experimental feed was supplemented with urea alone since prior studies with TMAO alone had not shown any positive effect on flesh colour. Testing together, all measurements, except hue, were significantly higher for rainbow trout fed commercial feed supplemented with urea (+TMAO) than for those fed commercial feed without any supplement (FIG. 2). A significant different flesh colour between fish in the 4 trials was also observed, but this was most certainly due to the great differences in fish size. Observation of the same increase in redness for fish fed experimental feeds containing a mix of urea and TMAO, and urea alone shows that the positive effect was due to the urea supplement alone. Finally, observation of a significant increase in both redness and yellowness, and therefore in chromaticity, but not in hue, indicates that supplement of dietary urea improves the retention of dietary astaxanthin.

EXAMPLE 3

Together with the periodic sampling of the fish for urea accumulation in example 1, all fish were weighed. During the handling of the rainbow trout vesicle in the skin was observed after 9 weeks. Since a statistic test surprisingly showed significantly more vesicle in the skin of fish fed control diet than diet supplemented with urea and TMAO (E1), every 6 weeks during the trial all fish (about 200 per pen) were recorded for vesicle. In all 10 samplings we observed a higher proportion of fish with vesicles among those fed control feed than among fish fed experimental diet (FIG. 3). This shows a highly significant ($p<0.0001$) and positive effect of the experimental feed. On average 10% of the control fish, whereas only 1.8% of the fish fed experimental feed had vesicles. By testing for differences in single samplings, we observed significantly less vesicles in 7 out of the 10 samplings. Earlier studies with TMAO had not shown such effect, but to test whether this was an effect of urea supplement alone, a trial was started (week 36) where the rainbow trout were fed urea supplement alone (E2). By sampling of the fish in week 40, we observed significantly less vesicle among these fishes than among the control fish (1.0% vs. 11.9%, FIG. 3). The vesicles developed into open sores after 36 weeks, but only among fish fed the control diet (6% vs. 0%; $p<0.05$).

Hence, during the trial which lasted for almost a year we observed a highly positive effect by supplementing the feed with urea. The positive result was quite surprising since Lunder (1992; "Winter ulcer in Atlantic salmon", dr.thesis, The Norwegian College of Veterinary Medicine) had isolated Vibrio spp. from manifest winter ulcers, and concluded from cohabitation experiments that the condition was transmissible, indicating that ulcers were due to a bacterial infection. In our experiment the vesicles developed into open sores only at the time of lowest sea temperature, which might suggest that dietary urea supplement also has a corresponding positive effect on winter ulcers in Atlantic salmon.

EXAMPLE 4

Figure 4:
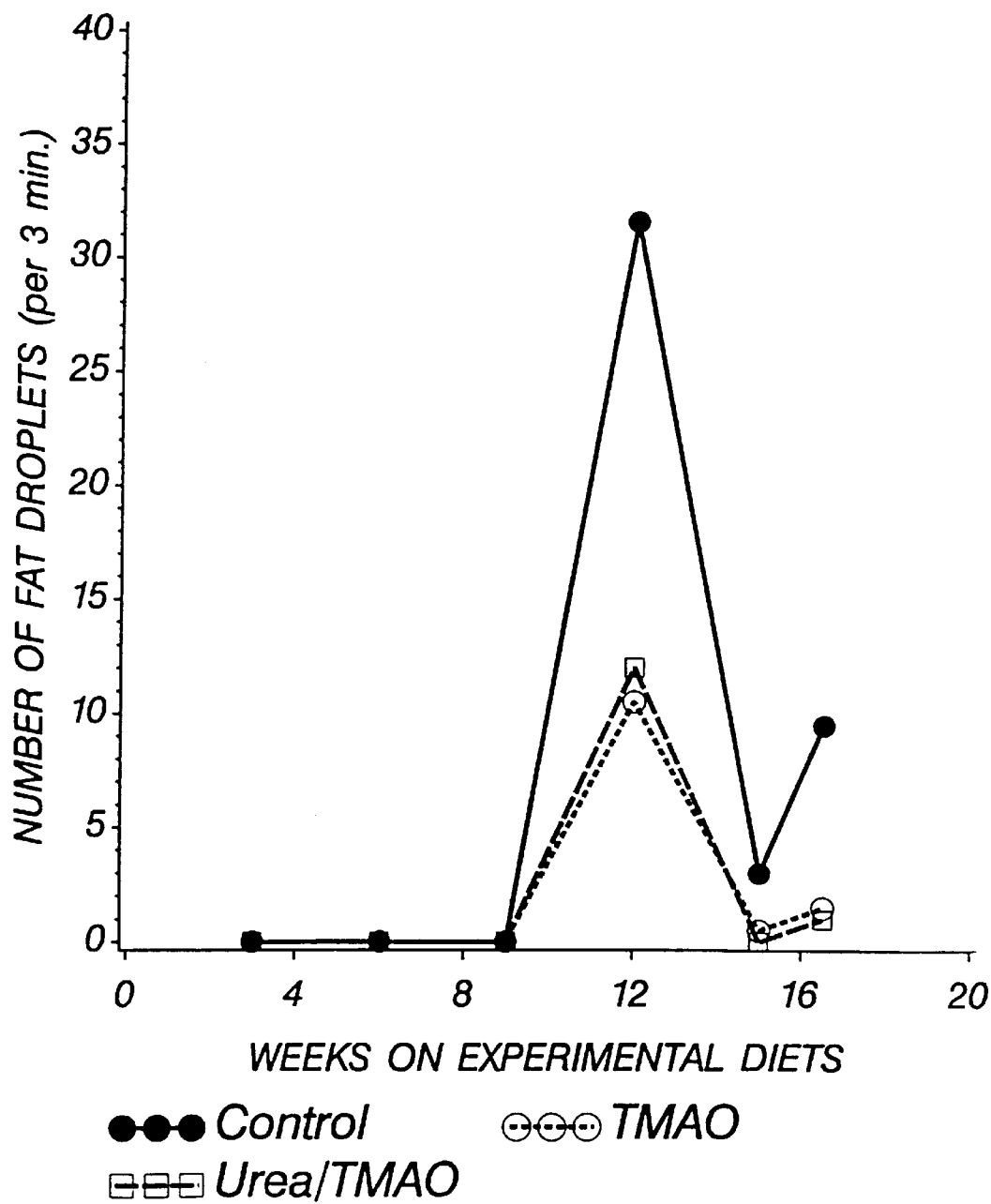

In the experiment with big rainbow trout (from 2.0 to 4.5 kg) in example 1 fat belching was recorded as number of fat droplets seen on the sea surface in each net pen about every 4 weeks. Beside a control feed, the rainbow trout was fed two experimental diets supplemented with TMAO alone or a mixed supplement of TMAO and urea. During the trial which lasted 17 weeks, we observed a significant effect of diets. Number of fat droplets varied significantly between weeks, but whenever droplets were seen it was always most in pens where the fish were fed control feed. During our 6 sampling times on average 7.3 fat droplets was observed from each net pen where the fish were fed control feed, whereas 2.1 or 2.2 droplets was recorded for fish fed TMAO or TMAO/urea, respectively (FIG. 4). It appears from FIG. 4 that the effect of supplement is almost the same for feeds with only TMAO addition as for feeds with addition of both TMAO and urea. This shows that the positive effect was due to TMAO and that the addition of urea did not interfere the TMAO's effect on fat belching.

By the present invention the inventors have succeeded in providing a feed, a method to provide fish of high quality and use of additional components to prepare said feed. By addition of urea and possibly TMAO or other methyl donating compounds like for instance betain and choline to a standard feed the quality related to colour of the fish flesh and development of ulcers on the skin is significantly improved. The invention therefore introduces a complete solution to several factors which are unfavourable for farmed fish compared to wild species and which reduce the production of farmed fish. This occur first of all as the colour of the fish flesh in trout and salmon is more strongly red than for farmed fish fed with other known feeds, and hence the retention of dietary astaxanthin is improved. Further, development of ulcers on the skin is kept to an absolute minimum. Fat belching is reduced by using the feed according to the invention. No harmful amounts of urea in the blood or the muscle in the fish are registered. The invention thus provides a feed which involves possibilities for low cost production of high quality fish.

We claim:

1. Feed for fish having salt-water tolerance, reduced tendency for formation of ulcers on the skin and improved effect of pigments in the feed, which comprises standard fish feed, 3–60 g urea/kg feed and 5–20 g trimethylamine oxide/kg feed.

2. Feed according to claim 1, which contains 3–30 g urea/kg feed.

3. A method for providing sea farmed fish having salt-water tolerance, reduced tendency for formation of ulcers on the skin and improved effect of pigments in the feed, which comprises feeding the fish with feed comprising standard fish feed, 3–60 g urea/kg feed and 5–20 g trimethylamine oxide/kg feed.

* * * * *

UNITED STATES PATENT AND TRADEMARK OFFICE
CERTIFICATE OF CORRECTION

PATENT NO. : 5,874,118

DATED : February 23, 1999

INVENTOR(S) : Kjell Arne Rørvik, et al.

It is certified that error appears in the above-identified patent and that said Letters Patent is hereby corrected as shown below:

Column 2, line 53, change "(FIG. 2)" to --(FIGS. 2A-2D)--.

Column 3, line 27, change "FIG. 2. Shows" to --FIGS. 2A-2D. Show--.

Column 3, line 41, change "FIG. 2 shows" to --FIGS. 2A-2D show--.

Column 5, line 12, change "(FIG. 2)" to –(FIGS. 2A-2D)--.

Signed and Sealed this

Twenty-seventh Day of July, 1999

Attest:

Q. TODD DICKINSON

*Attesting Officer*       *Acting Commissioner of Patents and Trademarks*